(12) United States Patent
Fahrner

(10) Patent No.: US 11,185,507 B2
(45) Date of Patent: Nov. 30, 2021

(54) COMPOSITIONS AND METHODS FOR INCREASING THE BIOAVAILABILITY OF ONE OR MORE COMPOUNDS

(71) Applicant: BOSTON BIOPHARM, INC., Boston, MA (US)

(72) Inventor: Richard L. Fahrner, Boxford, MA (US)

(73) Assignee: BOSTON BIOPHARM INC., Boston, MA (US)

(*) Notice: Subject to any disclaimer, the term of this patent is extended or adjusted under 35 U.S.C. 154(b) by 693 days.

(21) Appl. No.: 15/518,241

(22) PCT Filed: Oct. 8, 2015

(86) PCT No.: PCT/US2015/054766
§ 371 (c)(1),
(2) Date: Apr. 10, 2017

(87) PCT Pub. No.: WO2016/057839
PCT Pub. Date: Apr. 14, 2016

(65) Prior Publication Data
US 2017/0304204 A1 Oct. 26, 2017

Related U.S. Application Data

(60) Provisional application No. 62/061,603, filed on Oct. 8, 2014.

(51) Int. Cl.
| | | |
|---|---|---|
| *A61K 9/14* | (2006.01) | |
| *A61K 9/48* | (2006.01) | |
| *A61K 31/12* | (2006.01) | |
| *A61K 31/132* | (2006.01) | |
| *A61K 36/9066* | (2006.01) | |
| *A61K 47/34* | (2017.01) | |
| *A61K 47/36* | (2006.01) | |
| *A61K 47/44* | (2017.01) | |
| *A61K 47/26* | (2006.01) | |
| *A61K 9/08* | (2006.01) | |

(52) U.S. Cl.
CPC .............. *A61K 9/146* (2013.01); *A61K 9/145* (2013.01); *A61K 9/4866* (2013.01); *A61K 31/12* (2013.01); *A61K 31/132* (2013.01); *A61K 36/9066* (2013.01); *A61K 47/34* (2013.01); *A61K 47/36* (2013.01); *A61K 47/44* (2013.01); *A61K 9/08* (2013.01); *A61K 47/26* (2013.01); *A61K 2300/00* (2013.01)

(58) Field of Classification Search
None
See application file for complete search history.

(56) References Cited

U.S. PATENT DOCUMENTS

| | | |
|---|---|---|
| 2003/0235595 A1 | 12/2003 | Chen et al. |
| 2009/0044700 A1 | 2/2009 | Dietlin et al. |
| 2013/0225689 A1 | 8/2013 | Khamar et al. |

FOREIGN PATENT DOCUMENTS

| | | | |
|---|---|---|---|
| CN | 1 682 701 A | 10/2005 | |
| CN | 1 895 239 A | 1/2007 | |
| CN | 102 068 419 A | 5/2011 | |
| IN | 2012MU01218 * | 1/2014 | |
| WO | WO 2007/101551 A2 | 9/2007 | |
| WO | WO 2010/010431 A1 | 1/2010 | |
| WO | WO 2010/106191 A1 | 9/2010 | |
| WO | WO 2012/024405 A2 | 2/2012 | |
| WO | WO-2013012959 A1 * | 1/2013 | ........... A61K 9/1635 |
| WO | WO 2016/057839 | 4/2016 | |

OTHER PUBLICATIONS

Setthacheewakul, et al., Eur. J. Pharm. Biopharm., 76:475. (Year: 2010).*
Gugulothu, et al., Pharmaceutica Anal. Acta, 3:156. (Year: 2012).*
Supplementary European Search Report in Application No. EP 15 84 9218, dated Oct. 9, 2018.
Prasad, Sahdeo, Amit K. Tyagi, and Bharat B. Aggarwal. "Recent developments in delivery, bioavailability, absorption and metabolism of curcumin: the golden pigment from golden spice." *Cancer research and treatment: official journal of Korean Cancer Association* 46.1 (2014): 2-18.
Wu, Xuemei, et al. "Self-microemulsifying drug delivery system improves curcumin dissolution and bioavailability." Drug development and industrial pharmacy 37.1 (2011): 15-23.
Marczylo, Timothy H., et al. "Comparison of systemic availability of curcumin with that of curcumin formulated with phosphatidylcholine," *Cancer chemotherapy and pharmacology* 60.2 (2007): 171-177.
International Search Report for International Application No. PCT/US2015/054766, dated Feb. 6, 2015.

* cited by examiner

*Primary Examiner* — Michael Barker
(74) *Attorney, Agent, or Firm* — Gregory M. Howison

(57) ABSTRACT

Highly bioavailable compositions and related methods of improving the bioavailability of one or more compounds are disclosed. The compositions and methods disclosed herein may be employed to improve the bioavailability of poorly soluble or poorly bioavailable ingredients (e.g., curcumin) in a subject (e.g., a mammal).

13 Claims, 10 Drawing Sheets

COMPOSITIONS AND METHODS FOR INCREASING THE BIOAVAILABILITY OF ONE OR MORE COMPOUNDS

RELATED APPLICATION

This application claims the benefit of U.S. Provisional Application Ser. No. 62/061,603, filed Oct. 8, 2014, the entire teachings of which are incorporated herein by reference.

BACKGROUND OF THE INVENTION

The beneficial properties of certain compounds and the ability of such compounds to treat diseases or promote health may be limited by the poor solubility and the limited bioavailability of such compounds. For example, the potential benefits of curcumin (*Curcuma*), which has been used to treat certain diseases and promote human health as far back as 1937, has been hampered by poor oral bioavailability as a result of its poor oral absorption, high first pass metabolism and rapid systemic elimination. As a result, a significant fraction of orally administered curcumin is either not absorbed in the gastrointestinal tract and passes through the gastrointestinal tract and is excreted or is rapidly metabolized by the liver. Further contributing to its poor bioavailability, curcumin is not soluble at acidic pH and breaks down in solution at neutral or alkaline pH.

The safety and tolerability of curcumin has been evaluated and established in humans at doses up to 8 gram per day (Kanai, et al., *Cancer Chemother Pharmacol.* (2011) 68(1): 157-64; Dhillon, et al. *Cancer Res.* (2008) 14(14):4491-9.) The most promising clinical data focuses around the anti-inflammatory and anti-oxidative properties of curcumin (Lukita, et al. Shock (2002) 17: 399-403; Holt, et al. *Dig Dis Sci.* (2005) 50(11): 2191-3); however, the favorable properties of compounds such as curcumin remain limited as a result of such compounds' poor aqueous solubility or insolubility.

While methods and compositions for enhancing the delivery of compounds (e.g., poorly soluble natural dietary ingredients) have been previously disclosed, there remains a need for methods and compositions that are capable of enhancing the bioavailability and solubility of compounds. In particular, there remains a need in the art for compositions that are capable of enhancing the bioavailability of one or more compounds and, in particular, poorly soluble or insoluble compounds such as curcumin.

SUMMARY OF THE INVENTION

Disclosed herein are novel methods and compositions that are useful for improving the solubility of compounds, as well as highly bioavailable compositions that are useful for enhancing the delivery and absorption of such compounds in vivo. In certain embodiments, the present inventions relate to novel formulations of a compound (e.g., curcumin) that demonstrates improved bioavailability, improved gut solubility and/or improved enterocytic transport of the compound. In certain embodiments, the formulations disclosed herein result in significantly higher plasma concentrations of the compound (e.g., curcumin) and, in some instances, high concentrations of the compound's corresponding metabolic byproducts (e.g., curcumin metabolites), in each case relative to the unformulated compound or relative to formulations of such compounds described in the prior art. In certain embodiments, the curcumin formulations of the present invention were observed to yield a 1,200-fold greater plasma curcumin exposure in rats and about a 2,000 fold-increase in humans relative to unformulated curcumin.

In some embodiments, the present inventions encompass formulated compositions that comprise one or more compounds, wherein the composition demonstrates or is otherwise characterized by it enhanced bioavailability relative to the unformulated compound. Such compositions may further comprise one or more surfactants (e.g., one or more of Polysorbate 20, Polysorbate 80, Span 20, Cremophor EL, Cremophor RH 40 and Brij 58). In certain embodiments, such compositions may further comprise one or more lipid carriers (e.g., one or more of Gelucire 44/14, Gelucire 33/01, Gelucire® 50/13, Capryol 90, Peceol, Na Palmitate, Na Oleate, Acconon MC-8-2, Acconon C 44, Acconon CC-6, Vitamin E TPGS, Labrasol and TEA Oleate.) In certain embodiments, the lipid carrier is a single chain conjugated lipid (e.g., one or more of lauroyl macrogol-32 glycerides, caprylocaproyl macrogol-8 glycerides and sodium oleate). In some embodiments, the one or more lipid carriers (e.g., a single chain conjugated lipid) comprise about 10-80% w/w of the composition. In other embodiments, the one or more surfactants comprise about 10-90% w/w of the composition. In a preferred embodiment, one or more of the excipients and compounds that comprise the compositions disclosed herein are generally recognized as safe (GRAS).

The compositions and methods disclosed herein may be used to facilitate the delivery of a variety of compounds. In some embodiments, the compounds are poorly soluble or poorly bioavailable (e.g., curcumin). In some embodiments, the compounds comprise one or more dietary ingredients. For example, in certain embodiments, the compositions disclosed herein comprise one or more compounds selected from the group consisting of curcumin, methylsonfonyl-methane (MSM), Citrulline, Cinnamon, Glucoseamine, Hyaluronic acid, Chondroitin, CoQ10, Lutein, Quercetin, Berberine, Boswellia, Ginseng, Green Tea polyphenols, polyphenols, Shisandra, Aniracetam, Maca, Ginger, Arachidonic acid, *Cissus quadrangularis*, Dehydroepiandrosterone (DHEA), Hawthorn, S-Adenosyl Methionine (SAM), Glutathione, Ginkgo, Vitis, Resveratol, Silibum, Saw Palmetto, Black Cherry Extract, Curcurbita, Zeaxanthin, Capsicum, Ginger, Astaxanthin, Alpha Lipoic Acid, Vitamin D, Vitamin E, Echinacea Valerian, Rhodiola, Indole-3-Carbinol (I3C), Phenybut, Phosphatydlserine, Yohimbe, Black Tea Extract, Coleus, Bilberry, Cathepsin, Coleus, Linoleic acid, Lenoleic acid, Omega 9 (fatty acids), Astragalus, B-alanine, Ashwaganda, Olive leaf extract or polyphenols, Rosmarinic Acid, Alanylglutamine, *Rubus coreanus*, Sea Buckthorn, *Aronia melanocarpa*, Fenugreek, Catechins, Limonine, Oleamide, Bilberry extract, Raspberry ketones, Graviola, Phytosterols, Vinpocetine, Mucuna, St. Johns Wort, 33 Diindolylmethane, fish oil and krill oil. In certain embodiments, the compound is curcumin. In certain embodiments, the one or more compounds comprise about 1-30% w/w of the composition.

In one embodiment, the compositions disclosed herein comprise curcumin. An exemplary curcumin composition of the present invention comprises curcumin, a surfactant or an emulsifier such as Polysorbate 20 and one or more lipid carriers (e.g., one or more single chain conjugated lipids) such as Gelucire 44/14 and/or Capryol 90. In certain embodiments, the composition is formulated as a liquid, which may optionally be encapsulated. In certain embodiments, the composition may be formulated as a powder, which may optionally be encapsulated or tableted.

The compositions disclosed herein are characterized by their enhanced degree of bioavailability (e.g., relative to the unformulated compound or a comparator prior art formulation). For example, in certain embodiments, the composition has at least about 10-fold higher bioavailability relative to the unformulated compound (e.g., at least about 10-, 20-, 30-, 40-, 50-, 60-, 70-, 80-, 90-, 100-, 125-, 150-, 175-, 200-, 225-, 250-fold higher bioavailability relative to the unformulated compound). In other embodiments, the composition has at least about 500-fold higher bioavailability relative to the unformulated compound (e.g., at least about 500-, 600-, 700-, 750-, 800-, 850-, 900-, 950, 1,000-fold higher bioavailability relative to the unformulated compound). In some embodiments, the composition has at least about 750-fold higher bioavailability relative to the unformulated compound. In still other embodiments, the composition has at least about 1,000-fold higher bioavailability relative to the unformulated compound. In yet other embodiments, the composition has at least about 1,250-fold higher bioavailability relative to the unformulated compound. In some embodiments, the composition has at least about 1,500-fold higher bioavailability relative to the unformulated compound.

The compositions disclosed herein are also characterized by their enhanced or improved pharmacokinetic properties (e.g., AUC, $T_{max}$ and $C_{max}$). For example, in those embodiments where the composition comprises curcumin, upon administration or consumption of such composition to or by a subject (e.g., a mammal), the curcumin $T_{max}$ is about 30 minutes. In some embodiments, such compositions may comprise 100 mg of curcumin and, upon administration or consumption of the composition to or by a subject, the observed curcumin $AUC_{0-4}$ hours is at least 250 ng min/ml or at least 500 ng min/ml. In some embodiments, such compositions may comprise 200 mg of curcumin and, upon administration or consumption of the composition to or by a subject, the observed curcumin $AUC_{0-8}$ hours is at least 7,500 ng min/ml, at least 10,000 ng min/ml. or at least 14,500 ng min/ml. In some embodiments, such compositions may comprise 100 mg of curcumin and upon administration or consumption of the composition to or by a subject, the observed curcumin $C_{max}$ is at least about 7.5 ng/ml or at least about 15 ng/ml. In some embodiments, such compositions may comprise 200 mg of curcumin and upon administration or consumption of the composition to or by a subject, the observed curcumin $C_{max}$ is at least about 30 ng/ml, at least about 50 ng/ml, at least about 60 ng/ml or at least about 70 ng/ml.

Also disclosed herein are methods of treating a subject (e.g., a human) having 20 a disease (e.g., selected from the group of a proliferative disease, an autoimmune disease, an inflammatory disease, and a degenerative disease). Such methods generally comprise a step of administering the compositions disclosed herein to a subject (e.g., a mammal).

Also disclosed herein are methods of maintaining a healthy inflammatory response, a healthy pain response, joint health, promoting healthy memory and alertness, promoting healthy platelet function, promoting normal cell cycle growth, and supporting pancreatic islet health in a subject, such methods comprising a step of providing a composition of the present invention (e.g., a curcumin composition disclosed herein) and directing the subject to consume such composition for a period of time. In certain embodiments, the period of time can be two, three, four, five, six, seven, ten, twelve, fourteen, twenty one, twenty eight, thirty or more days. In certain embodiments the period of time can be 2 weeks, 3 weeks, 4 weeks, 5 weeks, 6 weeks, or 1 month, 2 months, 3 months or longer. In certain embodiments the period of time can be 1 year, 2 years, 3 years or longer. In certain embodiments, the methods disclosed herein include providing multiple daily doses of the composition and directing the subject to consume a daily dose of the composition. For example, the composition could be provided as a liquid or powder in capsule form and thirty capsules could be provided in a container, with instructions printed on the container to consume one capsule once a day.

Also disclosed herein are methods of increasing the bioavailability of a compound (e.g., curcumin). Such methods generally comprise the steps of: (i) combining the compound with one or more surfactants, one or more lipid carriers (e.g., single chain conjugated lipids) with or without solvents to form a mixture, which in certain embodiments may be a homogeneous mixture; (ii) heating the mixture, which in certain embodiments may be a homogeneous mixture, to at least about 60° C.; (iii) blending the mixture to homogeneity; and (iv) placing the homogeneous mixture in an acceptable dosage form, thereby increasing the bioavailability of the compound.

In certain embodiments, the present inventions relate to methods of preparing a curcumin composition, the method comprising: (i) combining the curcumin with one or more surfactants, one or more lipid carriers (e.g., single chain conjugated lipids) with or without solvent to form a mixture, which in certain embodiments may be a homogeneous mixture; (ii) heating the mixture, which in certain embodiments may be a homogeneous mixture, to at least about 60° C.; (iii) blending the mixture to homogeneity; and (iv) formulating the homogeneous mixture into an acceptable dosage form.

In certain embodiments, the lipid carriers disclosed herein (e.g., single chain conjugated lipids) have an hydrophilic-lipophilic balance (HLB) greater than 10. Exemplary lipid carriers may include Gelucire 44/14, Gelucire 33/01, Gelucire® 50/13, Capryol 90, Peceol, Na Palmitate, Na Oleate, Acconon MC-8-2, Acconon C 44, Acconon CC-6, Vitamin E TPGS, Labrasol and TEA Oleate. In certain embodiments, the lipid carrier is a single chain conjugated lipid. Such single chain conjugated lipids may be selected from the group consisting of lauroyl macrogol-32 glycerides, caprylocaproyl macrogol-8 glycerides, sodium oleate and combinations thereof. In certain embodiments, the one or more lipid carriers comprise about 10-80% w/w of the composition.

In certain embodiments, the one or more surfactants have an HLB greater than 10. Exemplary surfactants may be selected from the group consisting of polysorbate 20, polysorbate 80, Cremophor RH40, Solutol, Cremophor EL and combinations thereof. In some embodiments, the one or more surfactants are selected from the group consisting of Polysorbate 20, Polysorbate 80, Span 20, Cremophor EL, Cremophor RH 40 and Brij 58. In certain embodiments, the surfactant may comprise about 10-90% w/w of the composition.

In certain embodiments, the methods disclosed herein may further comprise a step of adding one or more excipients to the blended mixture, wherein the one or more excipients have a low HLB (e.g., an HLB less than 10). In some embodiments, the excipients may be selected from the group consisting of oleic acid, Peceol, Capryol 90, Capmul MCM C8 and Capmul MCM. In certain embodiments, the one or more excipients (e.g., lipid carriers, surfactants and/or excipients that comprise the formulations) are generally recognized as safe (GRAS).

In some embodiments, the methods disclosed herein may optionally comprise the use of a solvent (e.g., an organic solvent), such as one or more of ethanol or methanol; or a co-solvent such as one or more of polyethylene glycol and propylene glycol. In some embodiments, the composition is in the form of an emulsion. To the extent that the methods disclosed herein include the use of a solvent, such methods may also comprise a drying step of removing the solvent from the formulation. Accordingly, in certain aspects, the methods disclosed herein further comprise a drying step. Such a drying step may comprise one or more of spray drying, tray drying, lyophilization and/or vacuum drying.

In certain embodiments, the methods disclosed herein may be used to increase the bioavailability of one or more compounds. For example, methods of the present invention may be employed to increase the bioavailability of a compound by at least about four-fold relative to unformulated compound. In those embodiments where the compound is or comprises curcumin, such methods may be employed to increase the bioavailability of the curcumin by at least about fifty-fold relative to unformulated curcumin or by at least about one hundred-fold relative to unformulated curcumin. In certain embodiments, methods of the present invention may increase the absolute bioavailability of curcumin, relative to the same parenterally administered dose, by at least about 0.1, at least about 0.25 or at least about 1.0.

The compositions disclosed herein may be formulated in any acceptable dosage form (e.g., orally-administered dosage forms). For example, such compositions may by formulated in an acceptable dosage form such as a capsule, a tablet, an emulsion, a suspension, a solution, a lozenge and a reconstituable powder. In certain embodiments, such compositions are soluble in water. In some embodiments, such compositions are soluble in water, in simulated gastric fluids, in simulated intestinal fluids, as well as simulated fed state intestinal fluids.

In certain embodiments, upon administration or consumption of a curcumin composition of the present invention to or by a subject (e.g., a human subject), the composition produces at least a twenty-fold increase in a maximum plasma curcumin concentration relative to unformulated curcumin. Similarly, in certain embodiments upon administration or consumption by a subject (e.g., a mammal), the composition produces at least a twenty four-fold increase in a maximum plasma concentration of a curcumin glucoronide metabolite relative to unformulated curcumin. In certain embodiments, upon administration of or consumption by a subject the curcumin compositions disclosed herein reduce first pass metabolism of the curcumin relative to unformulated curcumin. In other embodiments, upon administration of or consumption by a subject, the curcumin compositions disclosed herein increase the area under the curve (AUC) of free curcumin relative to unformulated curcumin by at least twenty-fold. In still other embodiments, upon administration of or consumption by a subject, the curcumin compositions disclosed herein increase the $C_{max}$ of free curcumin relative to unformulated curcumin.

In certain embodiments, the compositions disclosed herein comprise about 100 mg of curcumin. In such embodiments, upon administration or consumption of such compositions to or by a subject (e.g., a human subject), an AUC of at least about 2,000 ng min/ml is observed in the subject. In other embodiments, upon oral administration or consumption of such compositions to or by a subject (e.g., a human subject) an AUC of at least about 3,000 ng min/ml is observed. In yet other embodiments, upon administration or consumption of such compositions to or by a subject (e.g., a human subject) an AUC of at least about 500 to 5,000 ng min/ml is observed.

In some embodiments, the methods and compositions disclosed herein may be used to improve the gut solubility of the compound. In other embodiments, the methods and compositions disclosed herein may be used to improve enterocytic transport of the compound.

The above discussed and many other features and attendant advantages of the present invention will become better understood by reference to the following detailed description of the invention when taken in conjunction with the accompanying examples.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1:
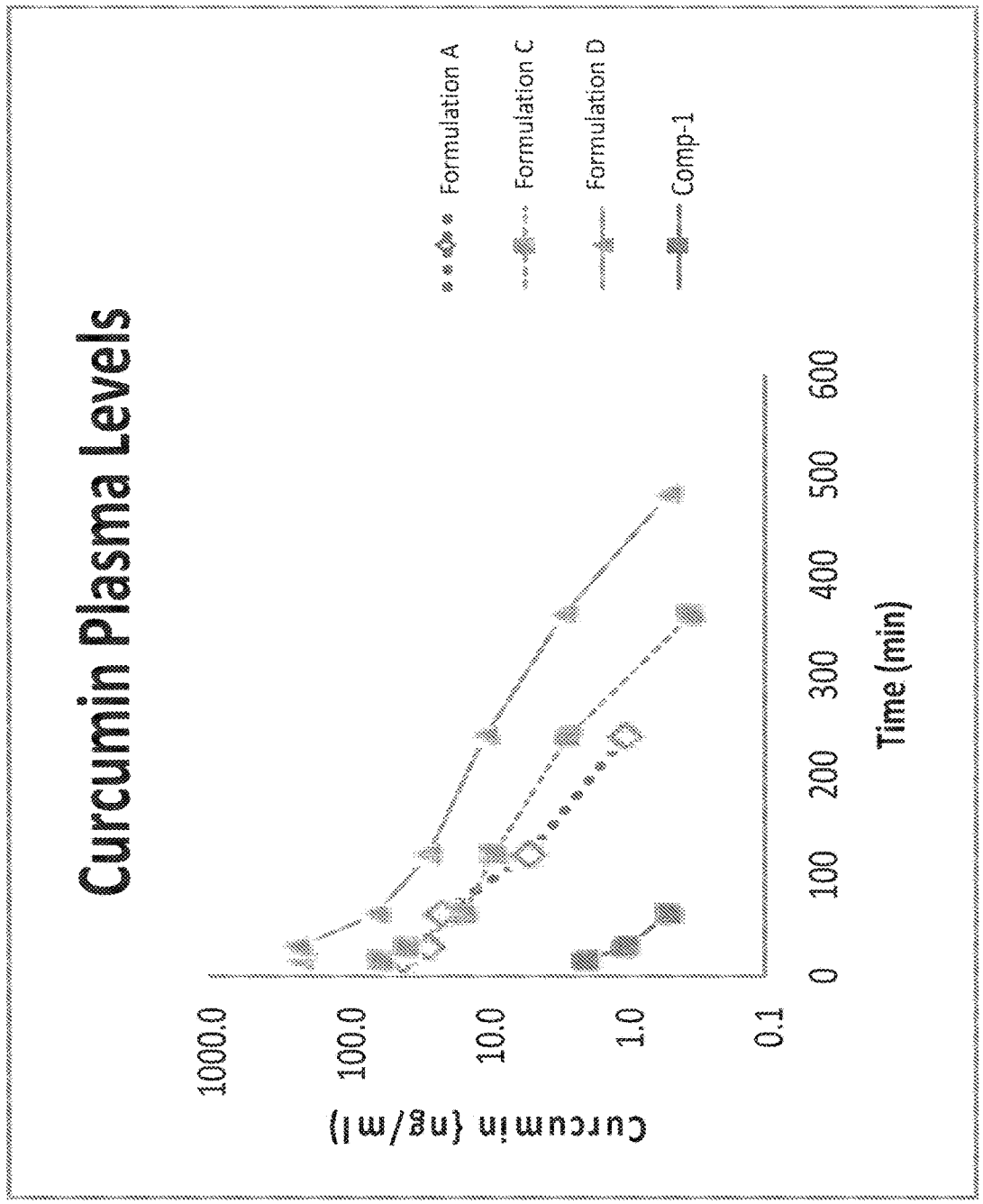
FIG. 1 illustrates plasma concentrations of curcumin in rats following the administration of a single dose of curcumin formulations of the present invention dosed at 100 mg/kg.
Figure 2:
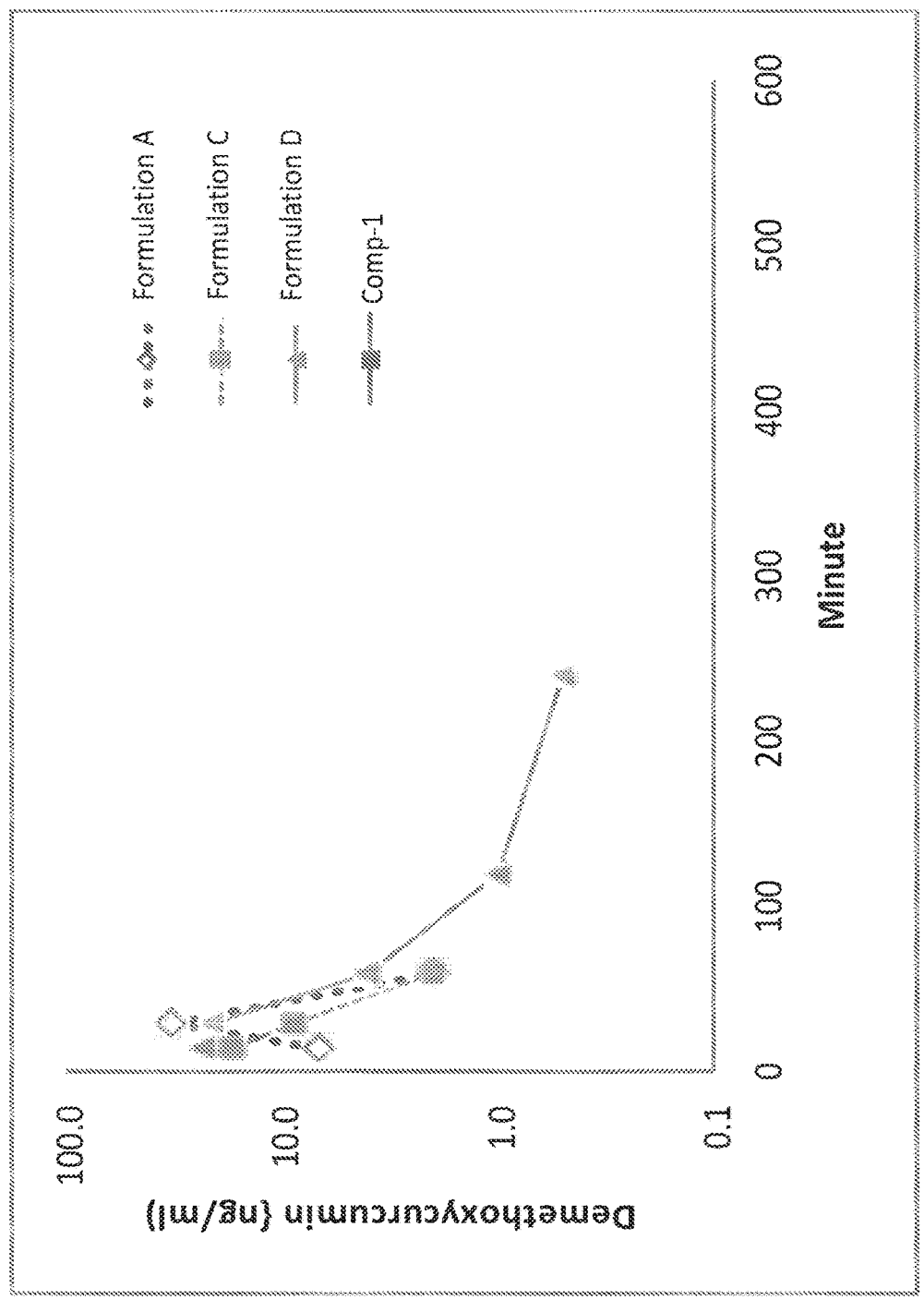
FIG. 2 illustrates plasma concentrations of the curcumin metabolite demethoxycurcumin in rats following the administration of a single dose of curcumin formulations of the present invention dosed at 100 mg/kg.
Figure 3:
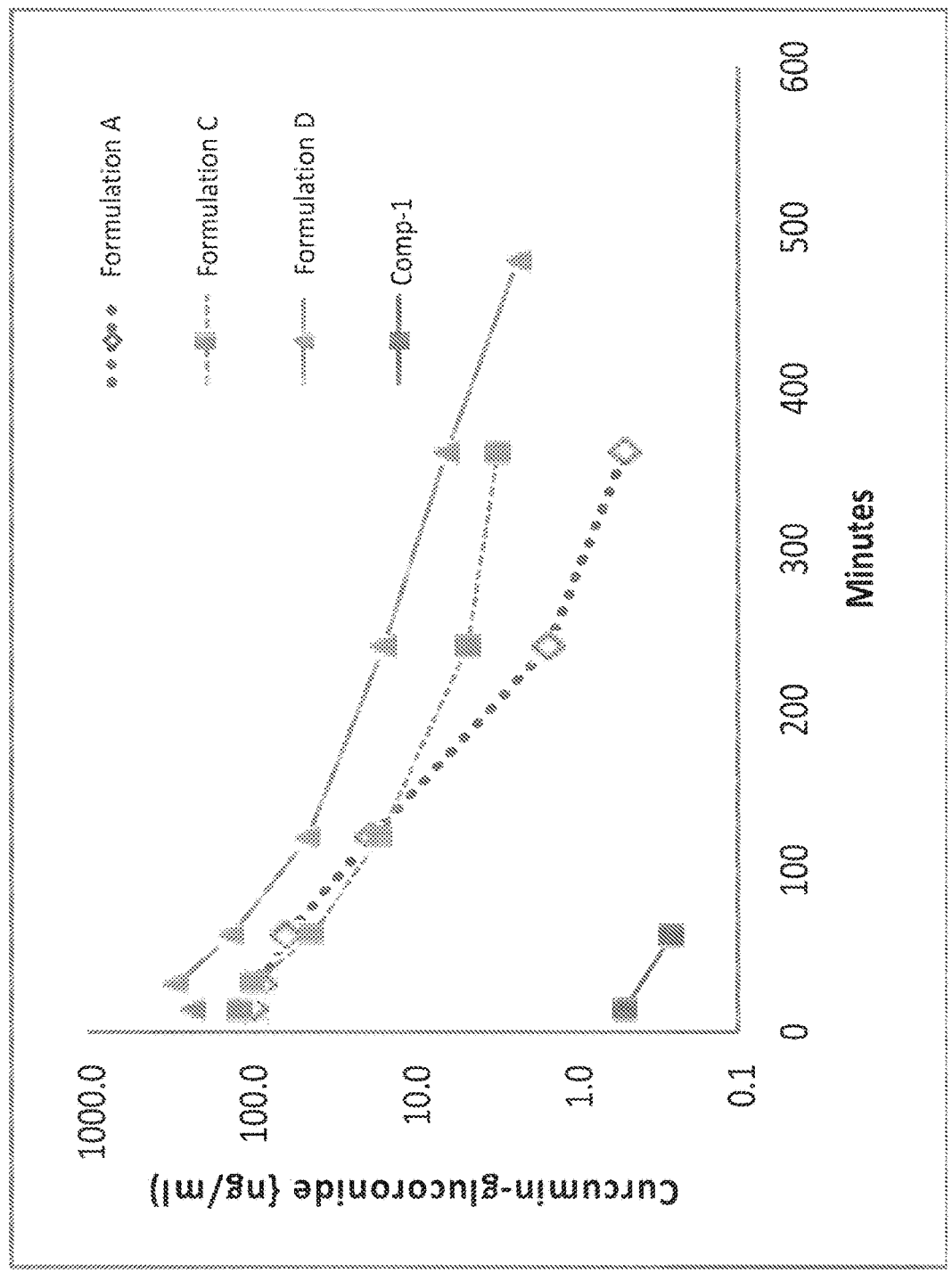
FIG. 3 depicts plasma concentrations of the curcumin metabolite curcumin-glucoronide in rats following the administration of a single dose of curcumin formulations of the present invention dosed at 100 mg/kg.
Figure 4:
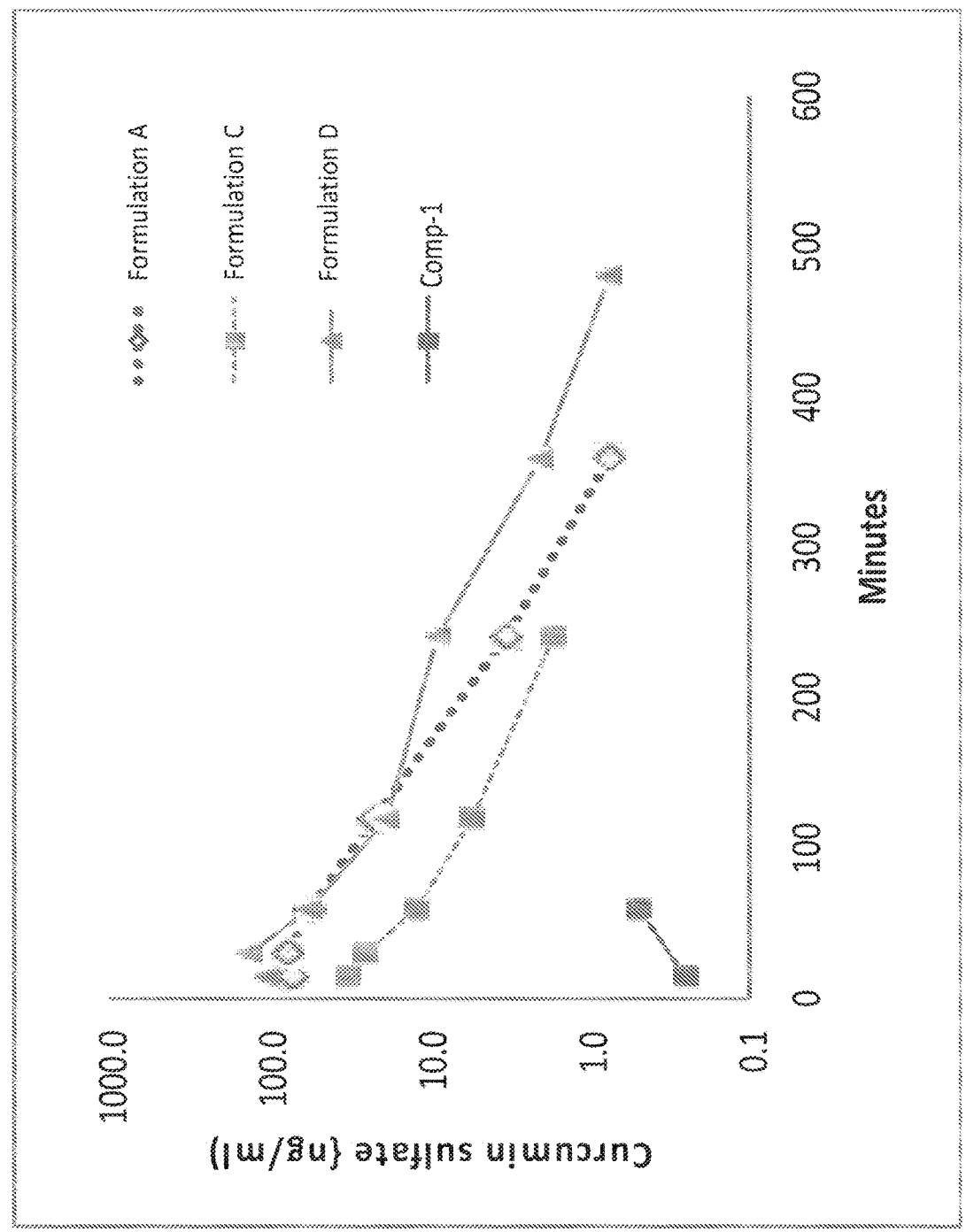
FIG. 4 illustrates plasma concentrations of the curcumin metabolite curcumin sulfate in rats following the administration of a single dose of curcumin formulations of the present invention dosed at 100 mg/kg.

The inventions disclosed herein generally relate to novel methods for improving the solubility (e.g., aqueous, gastric or intestinal solubility) of compounds (e.g., active pharmaceutical ingredients and/or natural dietary supplements), and to related compositions prepared in accordance with such methods. The compositions disclosed herein are characterized by the enhanced or improved bioavailability of the compounds contained therein and are useful treating diseases or conditions and/or for promoting, supporting and maintaining health, particularly in human subjects.

The methods and compositions disclosed herein may be used to enhance the bioavailability of one or more compounds. As used herein, the term "compound" generally refers to any composition or chemical or biological molecule or agent. In certain embodiments, the compound is a dietary ingredient, such as curcumin. In certain embodiments, such compounds have therapeutic properties.

As used herein, the term "dietary ingredient" refers to any vitamin, mineral, herb or other botanical, amino acid, or other dietary substance for use by a subject (e.g., a human subject) to supplement the diet by increasing the total dietary intake.

As used herein, the term "dietary supplement" refers to any orally administered dosage form (e.g., a tablet, pill, capsule, lozenge, powder or liquid) that contains a dietary ingredient and is intended to supplement the diet. In certain embodiments, the dietary supplement is consumed orally more than once daily (e.g., at least once a day). In certain aspects, the dietary supplement can be consumed by the subject for any period of time. For example, the period of time can be from about one, two, three, four days or more, up to about one month, two months, or more, up to about one year, two years, or more.

In certain embodiments, the compound is a curcuminoid (e.g., curcumin, demethoxycurcumin and bis-demethoxycurcumin), which are polyphenols commonly found in turmeric, a well known and often used spice derived from rhizome of *Curcuma* Tonga. Such curcuminoids provide turmeric its characteristic bright yellow color and are often added in small amounts as a color additive. The methods of the present invention may be utilized to significantly improve the bioavailability of curcumin and/or curcuminoids (e.g., 5-, 10-, 25-, 50-, 100-, 200-, 250-, 300-, 400-fold or more relative to unformulated curcumin or curcumin extract).

It should be noted that the methods and compositions of the present invention are not limited to curcumin, but rather may be used to improve the bioavailability of a wide-range of compounds. Exemplary compounds of the invention may comprise one or more compounds selected from the group consisting of methylsulfonylmethane (MSM), Citrulline, Cinnamon, Glucosamine, Hyaluronic acid, Chondroitin, CoQ10, Lutein, Quercetin, Berberine, Boswellia, Ginseng, Green Tea polyphenols, polyphenols, Shisandra, Aniracetam, Maca, Ginger, Arachidonic acid, *Cissus quadrangularis*, dehydropiandrosterone (DHEA), Hawthorn, S-adenosyl methionine (SAM), Glutathione, Ginkgo, Vitis, Resveratol, Silibum, Saw Palmetto, Black Cherry Extract, Curcurbita, Zeaxanthin, Capsicum, Astaxanthin, Alpha Lipoic Acid, Vitamin D, Vitamin E, Echinacea Valerian, Rhodiola, Indole-3-carbinol (I3C), Phenybut, Phosphatydlserine, Yohimbe, Black Tea Extract, Coleus, Bilberry, Casepsin, Coleus, Linoleic acid, Lenoleic acid, Omega 9 (fatty acids), Astragalus, B-alanine, Ashwaganda, Olive leaf extract, Rosmarinic Acid, Alanylglutamine, *Rubus coreanus*, Sea Buckthorn, *Aronia melanocarpa*, Fenugreek, Catechins, Limonine, Oleamide, Bilberry extract, Raspberry ketones, Graviola, Phytosterols, Vinpocetine, Mucuna, St. Johns Wort, 33 diindolylmethane, fish oil and krill oil. In some embodiments, the compounds are poorly soluble or poorly bioavailable. In some embodiments, the compounds comprise one or more dietary ingredients. In certain embodiments, the compound is curcumin. In certain embodiments, the one or more compounds comprise about 1-30% w/w of the composition.

The methods and compositions disclosed herein may be used to improve the bioavailability of one or more compounds, for example, by improving the water solubility of such compound, or by improving the gastric solubility of such compound, or by improving the intestinal solubility of such compound, or by improving enterocytic uptake and subsequent transport or by improving lymphatic transport of the compound. Such improved bioavailability of the compositions disclosed herein is reflected in the significantly higher plasma concentrations of the compound (e.g., curcumin) observed following administration to or consumption of such compositions by a subject. In certain aspects, the compounds disclosed herein (e.g. curcumin) and, in particular hydrophobic compounds, may be solubilized using surfactants, either with or without the aid of heat energy to disperse such compounds from the larger crystal lattice into individual molecules, thereby reducing the particle size leading to complete solubilization upon heating. In some embodiments, the methods disclosed herein render the compounds (e.g., hydrophobic compounds) disclosed herein completely soluble in water. In certain embodiments, the improved bioavailability of one or more compounds is reflected in the significantly higher concentrations of the compounds' corresponding metabolic byproducts (e.g., curcumin metabolites) relative to the unformulated compound or relative to formulations of such compounds described in the prior art. For example, as discussed in greater detail below, the curcumin formulations of the present invention yielded a 1,200-fold greater plasma curcumin exposure in rats and about a 2,000 fold-increase in humans relative to unformulated curcumin.

In certain embodiments, the compositions of the present invention enhance the bioavailability of the compounds comprised therein (e.g., relative to the unformulated compound or a comparator prior art formulation). In certain embodiments, the compositions of the present invention improve the bioavailability of a compound at least about 250-fold higher bioavailability, at least about 500-fold higher bioavailability, at least about 750-fold higher bioavailability, at least about 1,000-fold higher bioavailability, at least about 1,250-fold higher bioavailability or at least about 1,500-fold higher bioavailability relative to the unformulated compound.

The enhanced bioavailability of the compositions disclosed herein are reflected in the improved pharmacokinetic properties (e.g., AUC, $T_{max}$ and $C_{max}$) associated with such compositions, particularly relative to those compositions described in the prior art or the unformulated compound. For example, in those embodiments where the composition comprises curcumin, upon administration or consumption of such composition by a subject (e.g., a mammal), the curcumin $T_{max}$ is about 30 minutes. In some embodiments, such composition may comprise 100 mg of curcumin and, upon administration or consumption of the composition by a subject, the observed curcumin $AUC_{0-4}$ hours is at least 250 ng min/ml or at least 500 ng min/ml. In some embodiments, such composition may comprise 200 mg of curcumin and, upon administration or consumption of the composition by a subject, the observed curcumin $AUC_{0-8}$ hours is at least 7,500 ng min/ml, at least 10,000 ng min/ml. or at least 14,500 ng min/ml. In some embodiments, such compositions may comprise 100 mg of curcumin and upon administration or consumption of the composition by a subject, the observed curcumin $C_{max}$ is at least about 7.5 ng/ml or at least about 15 ng/ml. In some embodiments, such compositions may comprise 200 mg of curcumin and upon administration or consumption of the composition by a subject, the observed curcumin $C_{max}$ is at least about 30 ng/ml, at least about 50 ng/ml, at least about 60 ng/ml or at least about 70 ng/ml.

Also disclosed herein are methods of increasing the bioavailability of a compound (e.g., curcumin). Such methods generally comprise the steps of: (i) combining the compound with one or more surfactants, one or more lipid carriers (e.g., single chain conjugated lipids) and optionally one or more solvents to form a mixture; (ii) heating the mixture to at least about 60° C.; (iii) blending the mixture to homogeneity; and (iv) formulating the homogeneous mixture into an acceptable dosage form, thereby increasing the bioavailability of the compound.

In certain embodiments, the present inventions relate to methods of preparing a curcumin composition, the method comprising: (i) combining the curcumin with one or more surfactants, one or more lipid carriers (e.g., single chain conjugated lipids) and optionally one or more solvents to form a mixture; (ii) heating the mixture to at least about 60° C.; (iii) blending the mixture to homogeneity; and (iv) formulating the homogeneous mixture in an acceptable dosage form.

In certain embodiments, the lipid carriers disclosed herein (e.g., single chain conjugated lipids) have an HLB greater than 10. Exemplary lipid carriers may include Gelucire 44/14, Gelucire 33/01, Gelucire® 50/13, Capryol 90, Peceol, Na Palmitate, Na Oleate, Acconon MC-8-2, Acconon C 44, Acconon CC-6, Vitamin E TPGS, Labrasol and TEA Oleate. In certain embodiments, the lipid carrier is a single chain conjugated lipid. Such single chain conjugated lipids may be selected from the group consisting of lauroyl macrogol-32 glycerides, caprylocaproyl macrogol-8 glycerides, sodium oleate and combinations thereof. In certain embodiments, the one or more lipid carriers comprise about 10-80% w/w of the composition.

In certain embodiments, the one or more surfactants have an HLB greater than 10. Exemplary surfactants may be selected from the group consisting of polysorbate 20, polysorbate 80, Cremophor RH40, Solutol, Cremophor EL and combinations thereof. In some embodiments, the one or more surfactants are selected from the group consisting of Polysorbate 20, Polysorbate 80, Span 20, Cremophor EL, Cremophor RH 40 and Brij 58. In certain embodiments, the surfactant may comprise about 10-90% w/w of the composition.

The method disclosed herein may further comprise a step of adding one or more excipients to the blended mixture, wherein the one or more excipients have a low HLB (e.g., an HLB less than 10). In some embodiments, the excipients may be selected from the group consisting of oleic acid, Peceol, Capryol 90, Capmul MCM C8 and Capmul MCM. In certain embodiments, the one or more excipients (e.g., lipid carriers, surfactants and/or excipients that comprise the formulations) are generally recognized as safe (GRAS).

In some embodiments, the methods disclosed herein comprise the use of a solvent (e.g., an organic solvent), such as ethanol or methanol, as well as a co-solvent such as one or more of polyethylene glycol and propylene glycol. In some embodiments, the composition is in the form of an emulsion. In some embodiments, the composition is in the form of a solution or a suspension.

The methods disclosed herein may also comprise a drying step to remove the solvent from the formulation. Such a drying step may be selected from the group consisting of spray drying, lyophilization, tray drying and vacuum drying. In certain embodiments, the composition may be formulated as a powder, which may optionally be encapsulated or tableted. Alternatively, in other embodiments, the composition may be formulated as a liquid, which may optionally be encapsulated.

The methods disclosed herein may be used to increase the bioavailability of one or more compounds. For example, the methods of the present invention may be employed to increase the bioavailability of the compound by at least about four-fold relative to unformulated compound. In those embodiments where the compound comprises curcumin, such methods may be employed to increase the bioavailability of the curcumin by at least about fifty-fold relative to unformulated curcumin or by at least about one hundred-fold relative to unformulated curcumin. In those embodiments, the methods may increase the absolute bioavailability of the curcumin relative to the same parenterally administered dose by at least about 0.1, at least about 0.25 or at least about 1.0.

It should be understood that the methods disclosed herein may be employed to enhance the solubility (e.g., aqueous solubility, gastric solubility, and/or intestinal solubility, as well as fed state gastric and fed state intestinal solubility) of a number of compounds, active ingredients or dietary supplements. For example, such compound may be selected from the group consisting of curcumin, methylsonfonylmethane (MSM), Citrulline, Cinnamon, Glucoseamine, Hyaluronic acid, Chondroitin, CoQ10, Lutein, Quercetin, Berberine, Boswellia, Ginseng, Green Tea polyphenols, polyphenols, Shisandra, Aniracetam, Maca, Ginger, Arachidonic acid, *Cissus quadrangularis*, Dehydroepiandrosterone (DHEA), Hawthorn, S-Adenosyl Methionine (SAM), Glutathione, Ginkgo, Vitis, Resveratol, Silibum, Saw Palmetto, Black Cherry Extract, Curcurbita, Zeaxanthin, Capsicum, Ginger, Astaxanthin, Alpha Lipoic Acid, Vitamin D, Vitamin E, Echinacea Valerian, Rhodiola, Indole-3-Carbinol (I3C), Phenybut, Phosphatydlserine, Yohimbe, Black Tea Extract, Coleus, Bilberry, Casepsin, Linoleic acid, Lenoleic acid, Omega 9 (fatty acids), Astragalus, B-alanine, Ashwaganda, Olive leaf extract, Rosmarinic Acid, Alanylglutamine, *Rubus coreanus*, Sea Buckthorn, *Aronia melanocarpa*, Fenugreek, Catechins, Limonine, Oleamide, Bilberry extract, Raspberry ketones, Graviola, Phytosterols, Vinpocetine, Mucuna, St. Johns Wort, 33 diindolylmethane, fish oil, krill oil, and combinations of any of the foregoing. In certain embodiments, the one or more compounds comprise about 1-30% w/w of the composition.

The compositions disclosed herein may be formulated in any acceptable dosage form. In certain aspects, the dosage form is an orally administered dosage form. For example, such compositions may by formulated in an acceptable dosage form selected from the group consisting of a capsule, a tablet, a suspension, an elixir, a solution, a lozenge and a reconstituable powder. In certain embodiments, the present the compositions disclosed herein are formulated as a free flowing solid powder, which may be prepared by subjecting the liquid formulation to one or more techniques that may include encapsulation, nanospray drying, thin layer drying, freeze drying, using carriers such as, for example, microcrystalline cellulose, precipitated silica, Fujicalin, Nucelin, mannitol, hydroxypropyl methylcellulose (HPMC), arbocel, silica derivatives and combinations of any of the foregoing. In yet other embodiments, the compositions of the present invention are formulated as a semi solid gel, lotion or cream, which may be prepared by formulating the liquid formulation with suitable polymers, including, for example, hydroxypropyl methylcellulose (HPMC), isopropyl myristate, collagen, glycerol, cetyl alcohol, sterates of magnesium, zinc, calcium, carbopol and combinations of any of the foregoing. In certain embodiments, such compositions are soluble in water. In some embodiments, such compositions are soluble in simulated gastric fluids.

In certain embodiments, upon administration or consumption of a curcumin composition of the present invention by a subject (e.g., a human), the composition produces at least a twenty-fold increase in a maximum plasma curcumin concentration relative to unformulated curcumin. Similarly, in certain embodiments upon administration of or consumption by a subject. (e.g., a mammal), the composition produces at least a twenty four-fold increase in a maximum plasma concentration of a curcumin glucoronide metabolite relative to unformulated curcumin. In certain embodiments, upon administration of or consumption by a subject the curcumin compositions disclosed herein reduce first pass metabolism of the curcumin relative to unformulated curcumin, which may be determined by comparing the rate and level of formation of liver metabolites such as curcumin glucoronide and curcumin sulfate between unformulated and formulated curcumin. In other embodiments, the curcumin composition disclosed herein increases the AUC of free curcumin relative to unformulated curcumin by at least twenty-fold. In still other embodiments, upon administration of or consumption by a subject the curcumin compositions disclosed herein increase the $C_{max}$ of free curcumin relative to unformulated curcumin.

In certain embodiments, the compositions disclosed herein comprise about 100 mg of curcumin. In such embodiments, upon administration or consumption of such compositions by a subject (e.g., a human subject), an AUC of at least about 2,000 ng min/ml is observed in the subject. In other embodiments, upon consumption of such compositions by a subject (e.g., a human subject) an AUC of at least about 3,000 ng min/ml is observed.

In some embodiments, the methods and compositions disclosed herein may be used to improve the gut solubility of the compound. In other embodiments, the methods and compositions disclosed herein may be used to enterocytic transport of the compound.

Also disclosed herein are methods of treating a subject (e.g., a human) having a disease (e.g., selected from the group of a proliferative disease, an autoimmune disease, an inflammatory disease, and a degenerative disease). Such methods generally comprise a step of administering the compositions disclosed herein to a subject (e.g., a mammal), wherein the method comprises administering to the subject the compositions disclosed herein. In certain embodiments, the disease is a 25 proliferative disease (e.g., cancers, malignancies, benign growths and other conditions that result from hyperactivity or hyperplasia of somatic cells). In certain embodiments, the disease is an inflammatory disease (e.g., diseases is caused by the inflammatory response of the body to injurious effects of a body state and any concomitant pain, erythema, edema and/or tenderness. In certain embodiments, the disease is an autoimmune disease (e.g., disease resulting from an immune response against a self-tissue or tissue component, such as Crohn's disease and ulcerative colitis).

The methods of the present invention comprise the administration of an effective amount of the compositions disclosed herein to a subject affected by a disease or condition. For example, contemplated are methods of treating one or more diseases selected from the group of a proliferative disease, an autoimmune disease, an inflammatory disease and a degenerative disease, such methods comprising a step of administering the compositions disclosed herein to a subject in need thereof. As used herein, the term "subject" means any mammal, including humans. In certain embodiments of the present invention the subject is an adult or an adolescent human.

As used herein, the term "effective amount" means an amount sufficient to achieve a meaningful benefit to the subject (e.g., treating, modulating, curing, preventing and/or ameliorating the underlying disease). An effective amount of the compounds that comprise the compositions of the present invention may be generally determined based on activity of such compounds and the amount of such compounds that are absorbed by the subject following its oral administration. Generally, the amount of compound administered to a subject in need thereof will depend upon the characteristics of the subject and the severity of their disease. Such characteristics include the condition, general health, age, subjective symptoms, objective appearance, sex and body weight of the subject. One of ordinary skill in the art will be readily able to determine an effective amount depending on these and other related factors.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The entire contents of all of the references (including literature references, issued patents and published patent applications and websites) cited throughout this application are hereby expressly incorporated by reference.

The embodiments described herein will be further illustrated by the following Examples, which should not be construed as limiting.

EXAMPLES

Example 1

A curcumin liquid formulation referred to as Formulation A was prepared by mixing a surfactant (Polysorbate 20) and lipid carriers (Gelucire 44/14; Capryol 90) and an antioxidant (alpha-tocopherol [vitamin E]) using an overhead mixer and heated to between room temperature and 150° C. until homogenous. The excipient mixture may optionally contain an organic solvent such as ethanol.

Once the excipients were heated to temperature (90° C.), the powdered curcumin was slowly added to prevent clumping and accumulation on the sides of the vessel. Mixing continued at temperature (90° C.) until the mixture was fully homogenous and lacked cloudiness. Whether or not the optional organic solvent was present, vacuum was applied to degas the resulting mixture (remove entrapped air) and, to remove remaining solvent, if any. Full solvent removal may alternatively be accomplished by spray drying, tray drying, prilling, drum flaking or other similar process known in the art. The resulting mixture in liquid formulation was then cooled and filled into soft gel or hard gel capsules.

Example 2

A curcumin powder formulation referred to as Formulation B was prepared by mixing a surfactant (Polysorbate 20) and lipid carriers (Gelucire 44/14; Capryol 90) using an overhead mixer and heated to between room temperature and 150° C. until homogenous. The excipient mixture may optionally contain an organic solvent such as ethanol.

Once the excipients were heated to temperature (90° C.), the powdered curcumin was slowly added to prevent clumping and accumulation on the sides of the vessel. Mixing continued under heat until the mixture was fully homogenous and lacked cloudiness. Whether or not the optional organic solvent was present, vacuum was applied to degas the resulting mixture (remove entrapped air) and, to remove remaining solvent, if any. The mixture was held above the melting temperature of the mixture and a powdered absorbent added (e.g., Ribus Rice, hydroxypropyl methyl cellulose, carboxymethylcellulose, or a similar excipient) at 20-200 weight %. Alternatively, in certain embodiments, an additional dietary supplement substance may be added to yield a powdered curcumin formulation (e.g., curcumin, citrulline, methylsulfonomethane, egg shell membrane, or a similar supplement). The mixture was mixed to homogeneity and then allowed to cool to room temperature.

Once cooled, the mixture was milled to a powder. A flow agent was then added to the mixture (e.g., Ribus flow or magnesium stearate) to prevent the small powdered material from sticking together.

Example 3

The present investigators evaluated the performance of three unique curcumin formulations prepared in accordance with the previous examples (referred to herein as Formulations A, C and D) in a rat model and compared the pharmacokinetic characteristics of those formulations relative to a well-characterized and commercially-available phytosomal curcumin (PC) formulation.

Formulation A was prepared as follows: 175 mg of curcumin (184 mg of 95% curcumin), 779 mg of hydrogenated Soy phosphatidylcholine (HSoyPC) and 371 mg of non-hydrogenated Soy phophatidylcholine (Soy PC) (20:53.6:26.4 mole ratio of curcumin:HSoyPC:SoyPC) were dissolved in ethanol to a total lipid concentration of 94.66 mg/mL and a total curcumin concentration of 12.50 mg/mL. The mixture was heated to 65° C. and mixed until homogenous and clear with of visible particulates. The ethanol was then removed by lyophilization overnight. The formulation was then dissolved into 17.5 ml of phosphate buffered saline containing 0.225% (w %/w %) polysorbate 20. High sheer was then applied to the formulation utilizing a high powered sonicator set at 95% power for 30 seconds.

Formulation C was prepared as follows: 550 mg of 95% curcumin was mixed into 2.0 g Labrasol, 1.5 g polysorbate 20 and 1.5 g polyethylene glycol 400 (approximately 1 00 mg/ml curcumin). The mixture was heated to 90° C. for about 30 minutes until the oil was completely clear and allowed to cool. For dosing, the formulation was diluted 1:10 or 1 ml formulation+9 ml water and mixed (10 mg/ml curcumin) to form an emulsion.

Finally, Formulation D was prepared as follows: 550 mg of 95% curcumin was mixed into 1 g Gelucire 44/14, 1 g Peceol, 2.75 g polysorbate 20 and 0.25 g polyethylene glycol 400 (approximately 100 mg/ml curcumin). The mixture was heated to 90° C. for about 30 minutes until the oil was completely clear and allowed to cool. For dosing, the formulation was diluted 1:10 or 1 ml formulation+9 ml water and mixed (10 mg/ml curcumin) to form an emulsion.

Male Sprague-Dawley rats were purchased from Harlan and were acclimated to the facility for approximately two days prior to the start of the study. The rats were 10 weeks old and had an average body weight of 250 g. During the acclimation and study periods, animals were singly housed in a laboratory environment with temperatures ranging between 67–76° F. and relative humidity between 30-70%. Automatic timers provided a 12 hour light/dark cycle. Animals were allowed access ad libitum to fresh municipal tap water and to PharmaServ lab diet 5001 rodent chow except for an overnight fast prior to oral gavage dosing.

Animals were singly housed in shoe-box polycarbonate cages with wire tops, corncob bedding and suspended food and water bottles. Animal care, including room, cage and equipment sanitation, conformed to the guidelines cited in the Guide for the Care and Use of Laboratory Animals and the applicable standard operating procedures of Vivisource Laboratories, Inc (Waltham, Mass.). Each animal was observed daily from time of arrival to study end for clinical signs of ill health. Animals were identified by a distinct number at the base of the tail which specified the treatment group and individual animal number. After randomization, all cages were labeled with protocol number, group and animal numbers.

The three embodiments of the formulation referenced above and comparator phytosomal curcumin (PC) were supplied pre-formulated as aqueous emulsion. The emulsions were prepared for dosing by diluting in water to a purity corrected 10 mg/ml curcumin and vortexed for about 10 seconds to fully suspend. The PC was purchased at a local pharmacy and was diluted with water to 10 mg/ml based upon the label claim amount. High power sonication for 30 minutes at 50% power using a microtip sonicator was used which fully suspended the PC formulation. Dosing solutions were analyzed prior to dosing using the HPLC method described below and the doses were confirmed to be 100±5% of the dose target.

Formulations were administered to rats by oral gavage at a dose of 10 ml/kg or 100 mg/kg. Blood samples were collected after 0, 0.25, 0.5, 1, 2, 4, 6 and 8 hours and heparinized plasma was separated by centrifugation at 6,000 RPM for 5 min at 4° C. and stored at −80° C. until processed and analyzed.

Rat plasma (100 μL) was transferred by calibrated pipette into a 0.75 mL Eppendorf tube. 100 μL. of 1 M sodium chloride was added and the tube vortexed for 5 seconds. 350 μL ethyl acetate was then added and tubes mixed thoroughly for two minutes. Tubes Were centrifuged for 90 seconds at 13,000 RPM. 300 μL of the ethyl acetate layer were then transferred by pipette into a 96 well plate. The plate was dried under vacuum at 50° C., for 2 hours. 80 μL of diluent was added to each well to re-suspend the samples. The plate was sealed and vortexed on a plate vortexer for 2 minutes prior to injection.

Curcumin, demethoxy-curcumin and bisdemethoxy-curcumin levels, as well as metabolites of these molecules in plasma, were determined by using a Waters Acquity UPLC with PDA detection at 428 nm. Separations were performed on an Acquity BEH 1.0 mm×50 mm, C18 column at 50° C. (Waters Corp., Milford, Mass., USA). Mobile phase A was 0.1% trifluoroacetic acid in water and mobile phase B was 0.1% trifluoroacetic acid acetonitrile. Diluent consisted of 75% acetonitrile and 25% water (v/v). A 5 μL aliquot was injected from each well onto the reverse-phase column. Separation was achieved by linear gradient elution; 5-85% mobile phase B over 3.85 minutes. Flow rate was 0.35 mL/min. Peaks were integrated using Apex Track integration. Curcuminoid and metabolite concentrations were calculated by single point calibration utilizing a 25 ng/mL working standard. Peaks were identified by mass and by fragmentation. Masses and fragmentation patterns used are provided in Table 1 below.

TABLE 1

Molecular weights and fragmentation pattern used to identify the various curcumin species eluting in HPLC chromatograms and abbreviations used.

| Molecule | Abbreviation | Molecular Weight |
|---|---|---|
| Curcumin | C | 368 |
| Curcuminglucorinide | CG | 544 |
| Curcumin Sulfate | CS | 448 |
| Demethoxy Curcumin | DC | 338 |
| Demethoxy Curcumin-glucoronide | DCG | 514 |
| Demethoxy Curcumin-sulfate | DCS | 418 |
| bis-DemethoxyCurcumin | bDC | 308 |
| bis-DemethoxyCurcumin-glucoronide | bDCG | 484 |
| bis-DemethoxyCurcumin-Sulfate | bDCS | 388 |

The linear range of the method was confirmed from 3-1000 ng/mL with a 0.9998 correlation coefficient. The LOQ of the method was determined to be 3 ng/mL while the LOD was 1 ng/mL with a signal to noise of 10 to 1 and 3 to 1 respectively. Extraction efficiency was determined by spiking a known standard into rat plasma to achieve a final concentration across the linear range of the method (5-500 ng/mL). Method accuracy was determined at three levels 5 ng/mL, 25 ng/mL, and 250 ng/mL. Three injections at each level were performed and the % RSD at each level was less than 5%.

Serum levels of curcumin and its metabolites demethoxycurcumin, bisdemethoxycurcumin, as well as the glucoronide and sulfate metabolites of the curcuminoids were directly quantitated in rat plasma without enzymatic manipulation. As illustrated in FIGS. 1-4, time dependent serum concentrations of curcumin (FIG. 1), demethoxycurcumin (FIG. 2), curcuminglucoronide (FIG. 3) and curcuminsulfate (FIG. 4) were each measured. Bisdemethoxycurcumin as well as the metabolites of bisdemethoxycurcumin and demethoxycurcumin were observed but were at or below the limit of quantitation and are therefore not included. A summary of the observed pharmacokinetic properties is provided in Table 2, below.

TABLE 2

AUC observed for various species after 100 mg/kg single dose PK in rats

| Component | Formulation C | Formulation A | Formulation D | PC |
|---|---|---|---|---|
| Free Curcumin | 3113 | 6386 | 13526 | 60 |
| Curcumin Glucoronide | 7300 | 7161 | 21069 | 15 |
| Curcumin Sulfate | 2020 | 7170 | 9354 | 24 |

Most published studies evaluating the bioavailability of curcumin rely on enzymatic treatment to convert metabolized curcumin (curcumin glucoronide and curcumin sulfate) back into curcumin and then report the "total curcuminoid" plasma exposure. In the pharmacokinetic studies described herein, an unexpected and surprisingly high concentration of plasma curcumin was observed without enzymatic treatment of the samples. Samples were spot checked and the recovery standard checked to verify the observed results. The pharmacokinetics of the impurities while at much lower levels follow the curcumin levels and most importantly the metabolite levels are high and their peak levels lag the parent molecule slightly. The present investigators observed yellow-green urine in the rats administered the Formulation A and D two hours after administration, which was not observed for the other dosing groups, further evidencing the high plasma curcumin levels observed following administration of the Formulations A and D.

Figure 10:
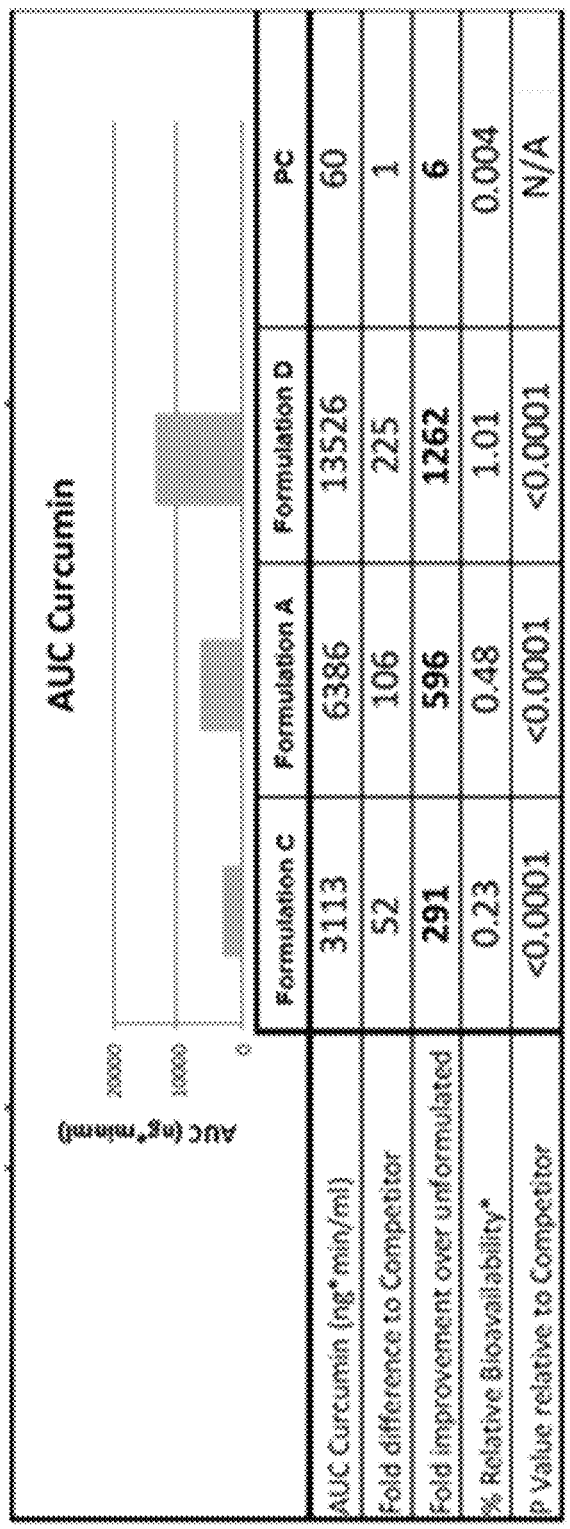
FIG. 10 illustrates a comparison of curcumin formulations of the present invention (Formulations A, C, and D) data relative to competitor phytosomal curcumin (PC) formulation. Bioavailability improvement over unformulated is calculated from published data.

In comparison to the phytosomal curcumin formulation (PC), an improvement in bioavailability was observed in each of the three formulations evaluated, not only for curcumin but also for the major metabolites, curcumin glucoronide and curcumin sulfate (Tables 2 and FIG. 10). Relative to the comparator PC, up to a 225-fold improvement in plasma curcumin levels and a 1,300-fold improvement compared to unformulated curcumin (calculated using published data at Marczylo, et al., *Cancer Chemother. Pharmacol* (2007) 60(2): 171-177) were observed following the administration of the curcumin formulations of the present invention.

The AUC of the curcumin of the formulations of the present invention and the PC were compared against the AUC from a known rapidly metabolized molecule that was dosed intravenously. This comparison yielded a percent relative bioavailability that is set forth in FIG. 10, which shows that the formulations of the present invention are superior to the PC.

Example 4

Several n=1 type human studies were undertaken to evaluate the basic pharmacokinetics of the curcumin formulations of the present invention, generally these studies were 8 hours in duration. Various amounts of such curcumin formulations (e.g., Formulations A and D) in a capsule were consumed by the subjects. Dosage forms were analyzed prior to dosing using the HPLC method described below and doses were confirmed to be 100±5% of the dose target. Blood was drawn by finger lancing yielding between 200 to 500 μl of blood per time point. Samples were immediately centrifuged at 20000×g for 10 minutes at 4° C. The serum was transferred to an Eppendorf tube and 3:1 volume of ethyl acetate was added. The sample was bath sonicated for 10 minutes and then centrifuged at 20000×g for 10 minutes at 4° C. The ethyl acetate layer was then transferred to a glass vial. Two additional ethyl acetate washes were performed in a similar manner and the ethyl acetate layers were pooled in a glass vial. Samples were then dried using a Genevac EZ Plus2. Samples were then resolublized by adding 100 μL methanol and sonicating in a bath sonicator for 10 minutes.

Samples were assayed using an Agilent 1260 Infinity HPLC and peaks were quantitated using PDA detection at 430 nm. Peak identities were confirmed by single-quadrupole mass spectrometry of each peak (Masses provided in Table 1). Separations were performed using an Agilent PoroShell SB-C18 4.6×150 2.7 μm column. Mobile phase A was 0.1% formic acid in water and mobile phase B was 0.1% formic acid in 50% acetonitrile/50% methanol. Diluent consisted of 75% acetonitrile and 25% water (v/v). A 5 μL aliquot was injected from each well onto the reverse-phase column. Separation was achieved by linear gradient elution; 5 to 85% mobile phase B over 3.85 minutes. Flow rate was 0.35 mL/min. Curcuminoid and metabolite concentrations were calculated by single point calibration against a standard curve utilizing a 25 ng/mL working standard.

The linear range of the method was confirmed from 0.03-1000 ng/mL. The correlation coefficient was 0.9998. The LOQ of the method was determined to be 0.03 ng/mL while the LOD was 0.0005 ng/mL. Signal to noise of 10 to 1 and 3 to 1 respectively. Extraction efficiency was determined by spiking a known standard into rat plasma to achieve a final concentration across the linear range of the method (0.03 to 1000 ng/mL). Method accuracy was determined at 6 levels: 0.1 ng/mL, 0.5 ng/mL, 1.0 ng/mL, 5.0 ng/mL, 25 ng/mL and 250 ng/mL. Three injections at each level were performed and the % RSD at each level was less than 5%.

Figure 5:
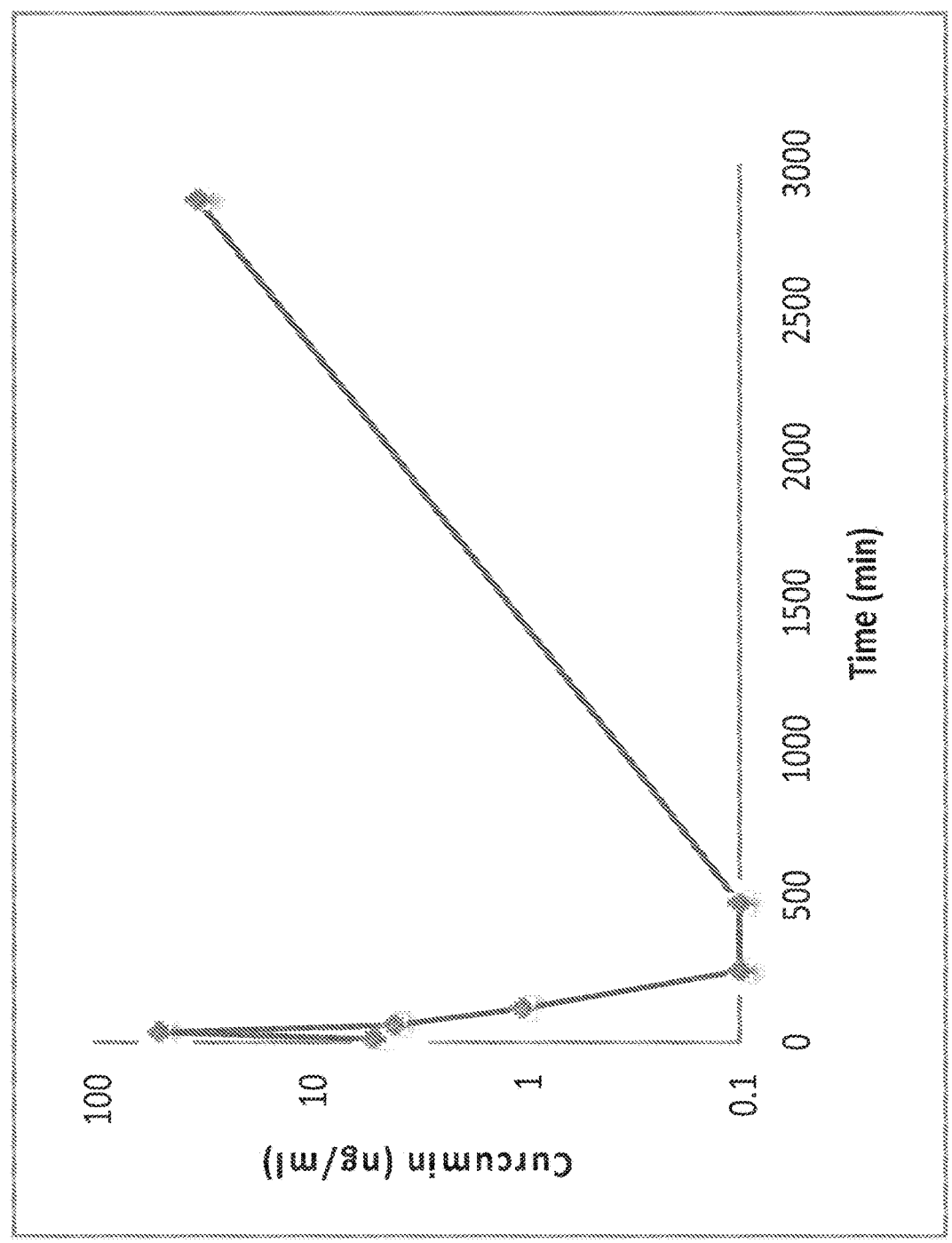
FIG. 5 depicts the time-dependent plasma curcumin concentrations following the consumption of a single 200 mg dose of a curcumin formulation of the present invention by a human subject (n=1). Curcumin $AUC_{0-48}$ hours was 41,183 ng min/ml.

The results of the human studies are illustrated in FIGS. 5-9 and in Table 3 below. FIG. 5 illustrates the time-dependent plasma concentrations of curcumin following the consumption of a single 200 mg dose of the liquid curcumin formulation by a human (n=1). The total curcumin at $AUC_{0\text{-}48}$ hours was 41,183 ng min/ml.

TABLE 3

AUC observed for various curcumin formulations in humans

| | Formulation | | | |
|---|---|---|---|---|
| | Formulation D | Formulation A | Formulation A | Formulation A |
| State | Liquid | Liquid | Liquid | Powder |
| Dose | 200 mg | 100 mg | 200 mg | 200 mg |

TABLE 3-continued

AUC observed for various curcumin formulations in humans

| | Formulation | | | |
|---|---|---|---|---|
| | Formulation D | Formulation A | Formulation A | Formulation A |
| Study Duration (Hours) | 48 | 4 | 8 | 9 |
| AUC (ng min/ml) | 41183 | 595 | 8966 | 14626 |
| $T_{max}$ (min) | 30 | 30 | 30 | 30 |
| $C_{max}$ (ng/ml) | 72.3 | 8.7 | 32.8 | 64.4 |

Figure 6:
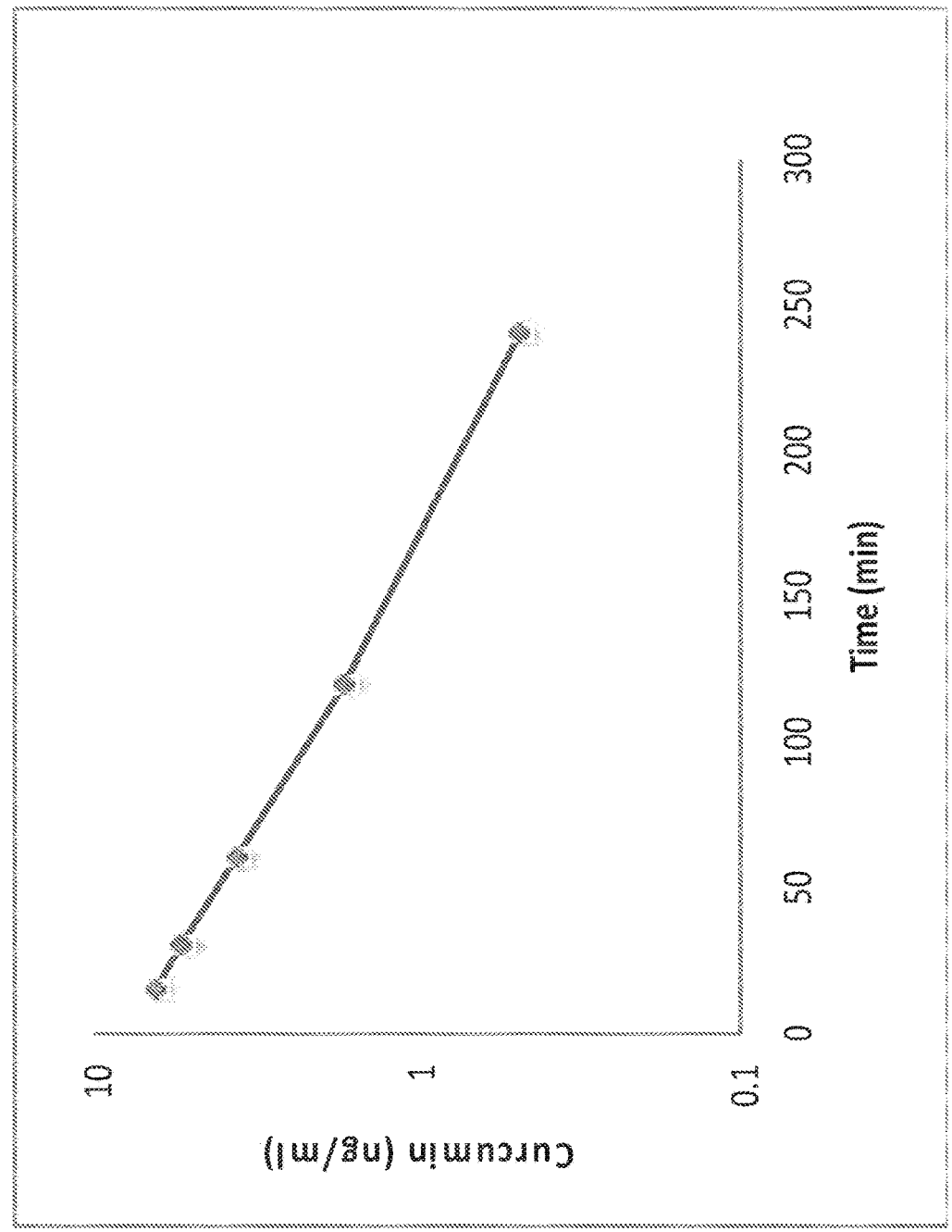
FIG. 6 illustrates the time-dependent plasma curcumin concentrations following the consumption of a single 100 mg oral dose of a curcumin formulation of the present invention by a human subject (n=1). Curcumin $AUC_{0-4}$ hours was 595 ng min/ml.

FIG. 6 illustrates the results of Human study 2 and presents time-dependent plasma curcumin concentrations after a single 100 mg oral dose of a liquid curcumin formulation in a human (n=1). The observed curcumin $AUC_{0\text{-}4}$ hours was 595 ng min/ml.

Figure 7:
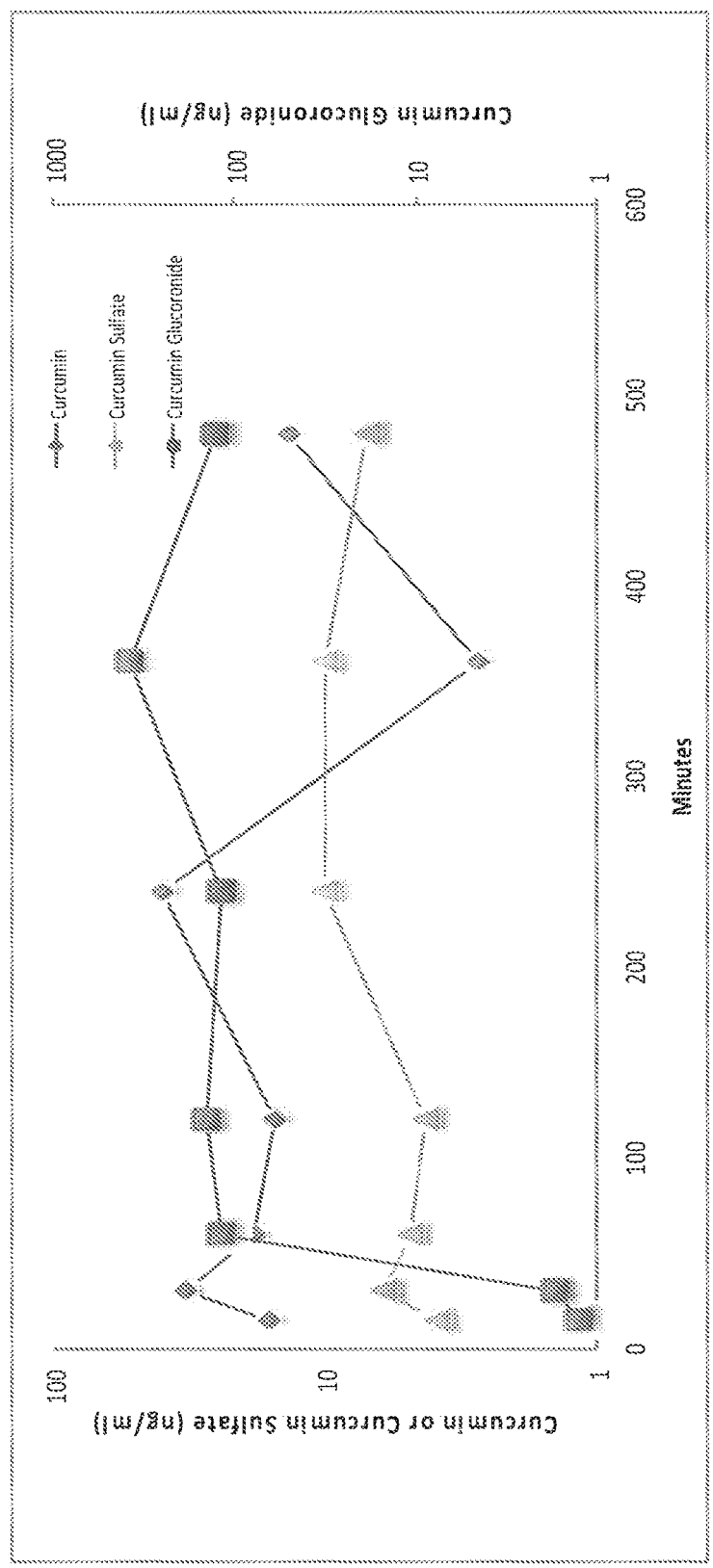
FIG. 7 illustrates the time-dependent plasma concentrations of curcumin and its metabolites curcumin-glucoronide and curcumin sulfate following the consumption of a single 200 mg dose of a curcumin formulation of the present invention by a human subject (n=1). Curcumin $AUC_{0-8}$ hours was 8,966 ng min/ml.

FIG. 7 depicts the results of Human study 3 and shows time-dependent plasma curcumin, curcumin glucoronide and curcumin sulfate concentrations after a single 200 mg oral dose of a liquid curcumin formulation in a human (n=1). The observed curcumin $AUC_{0\text{-}8}$ hours was 8,966 ng min/ml.

Figure 8:
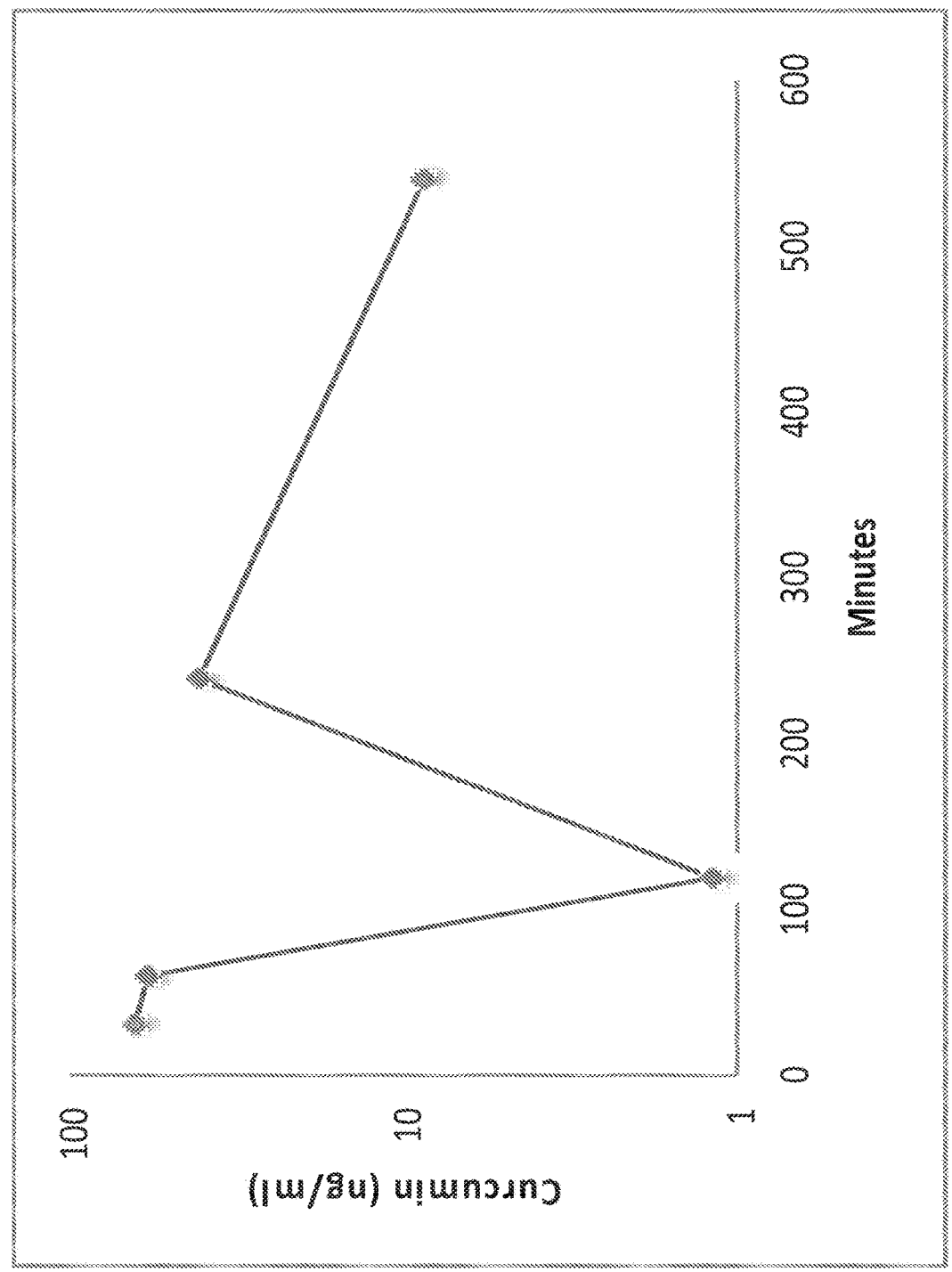
FIG. 8 depicts the time-dependent plasma concentrations of curcumin following the consumption of a single 200 mg dose of a curcumin formulation of the present invention by a human (n=1). Curcumin metabolites were not quantitated in this study. Curcumin $AUC_{0-8}$ hours was 14,626 ng min/ml.

FIG. 8 illustrates the results of Human study 4 and shows time-dependent plasma curcumin concentrations after a single 200 mg oral dose of the curcumin powder formulation of the present invention in a human (n=1). Metabolites were not quantitated in this study. The observed curcumin $AUC_{0\text{-}8}$ hours was 14,626 ng min/ml.

Figure 9:
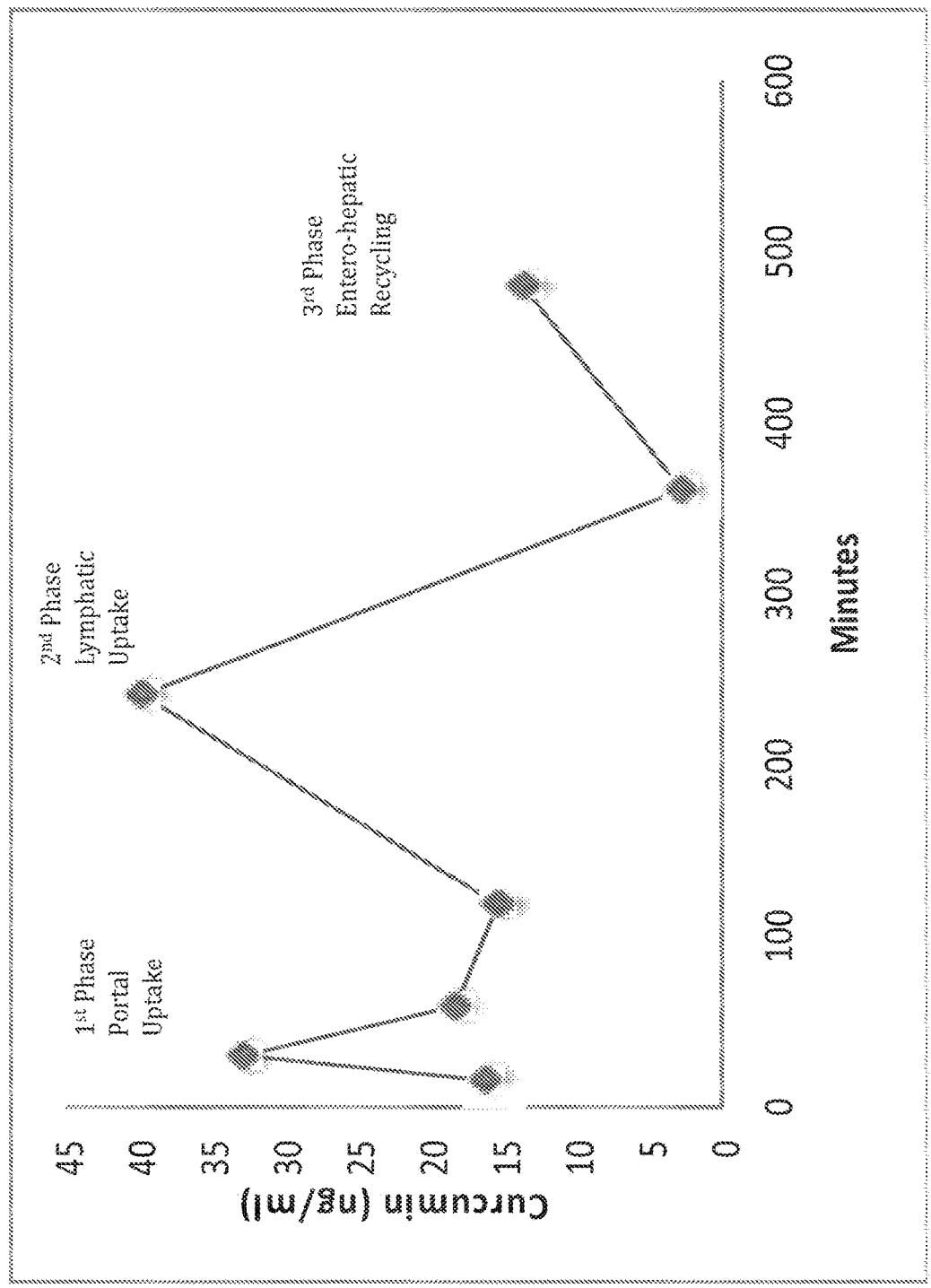
FIG. 9 illustrates the time-dependent plasma concentrations of curcumin following the consumption of a single 200 mg dose of a curcumin formulation of the present invention by a human subject (n=1). As illustrated, curcumin uptake has three distinct phases: $T_{max1}$ at 30 minutes (early portal uptake), $T_{max2}$ at 4 hours (lymphatic uptake), and $T_{max3}$ at 8 hours (enterohepatic recycling).

The forgoing human studies demonstrate that high plasma concentrations of curcumin may be achieved using the curcumin formulations of the present invention. As illustrated in FIG. 9, the uptake of curcumin from the curcumin formulations of the present invention was multiphasic and most likely represents traditional (portal) uptake ($T_{max1}$=30 minutes), lymphatic uptake ($T_{max2}$=4 hours), and a late uptake event that suggests enterohepatic recycling ($T_{max3}$=8 hours).

As illustrated in Table 4 below, the pharmacokinetic properties observed following consumption of the curcumin formulations of the present invention were compared to published data corresponding to other commercially-available formulations of curcumin. To facilitate comparison, the published data was dose normalized to the Formulation A dosing. The BioCurc formulation of the present invention was calculated using only the plasma curcumin levels and summing the AUC from all metabolites to be able to compare to other formulations. Only THERACURMIN has published bioavailability data for plasma curcumin and, as illustrated in Table 4 below, the curcumin bioavailability observed following administration of the curcumin Formulation A of the present invention was 75 times greater relative to such THERACURCUMIN product. Comparing the total curcuminoid bases, the bioavailability of the curcumin Formulation A of the present invention was 420 times higher than unformulated curcumin and between 9 and 53 times higher than the MERIVA, THERACURMIN and CURCUWIN comparator products.

TABLE 4

BioCurc bioavailability from Human Study 3 compared to published data from other curcumin formulations.

Relative Absorption in Humans

| Component | BioCurc | Cavamax W8 | BCM-$_{95}$ | TheraCurmin | CurcuWin | Meriva | C3 | Unformulated Curcumin |
|---|---|---|---|---|---|---|---|---|
| Manufacturer | BBP | Wacker Chemie | DolCas Biotech | Integrative Therapeutics | OmniActive | Indena | Sabinsa | N/A |
| Formulation Description | Proprietary | Cyclodexrin | 7-9% Tumerone | 46% glycerin, 4% Gum ghatti polysaccharides, 38% water | Triglycerides Carrier (Cellulose) Antioxidant | SoyPC Particle Pytosome | Bioperine | N/A |
| API Load (%) | 3-35 | 10-30 | 86 | 10 | 20 | 20 | 12 | 100 |
| Curcumin (ng * hr/ml)$^a$ | 325.9 | N/A | Not Observed | 4.36 | Not Observed | Not Observed | Not Observed | Not Observed |
| Total Curcuminoids after enzyme treatment | 1847 | N/A | 5.8 | >4.36 | 202.1 | 34.7 | Not Observed | 4.4 |
| Curcumin Exposure Relative increase over unformulated (fold) | >2060 | N/A | N/A | >27.6 | N/A | N/A | N/A | N/A |
| Total Curcuminoid Exposure Relative increase over unformulated (fold) | 420 | N/A | 1 | >27.6 | 46 | 8 | N/A | 1 |

DISCUSSION

The present inventor has developed several new and improved classes of curcumin formulations that are characterized by their markedly improved bioavailability, as demonstrated in both rats and humans. In addition to the likely health benefits that these formulations may afford, these formulations appear to have great utility as they can be formulated as both a liquid and solid, can be mixed with other ingredients and increase the ingredient density to reduce pill burden. Further, the formulations offer distinct manufacturing advantages because the post manufacturing clean-up is easy.

What is claimed is:

1. A composition comprising one or more dietary ingredient compounds, one or more surfactants and one or more lipid carriers; wherein the one or more compounds comprise curcumin; wherein the one or more surfactants comprise Polysorbate 20; wherein the one or more lipid carriers comprise Gelucire 44/14 and Capryol 90; and wherein the composition has at least about 1,250-fold higher bioavailability relative to the unformulated compound.

2. The composition of claim 1, wherein the one or more lipid carriers further comprise a lipid carrier selected from the group consisting of Gelucire 33/01, Gelucire 50/13, and Labrasol.

3. The composition of claim 2, wherein the one or more lipid carriers comprise about 10-80% w/w of the composition.

4. The composition of claim 1, wherein the one or more dietary ingredient compounds comprise about 1-30% w/w of the composition.

5. The composition of claim 4, wherein the one or more surfactants comprise about 10-90% w/w of the composition.

6. The composition of claim 1, wherein the composition is in a dosage form selected from the group consisting of a liquid, a powder, a capsule and a tablet.

7. The composition of claim 1, wherein the composition comprises curcumin; and wherein upon consumption of the composition by a subject, T max is about 30 minutes.

8. The composition of claim 1, wherein the composition comprises 100 mg of curcumin; and wherein upon consumption of the composition by a subject, the observed curcumin $AUC_{0-4}$ hours is at least 250 ng min/ml.

9. The composition of claim 1, wherein the composition comprises 100 mg of curcumin; and wherein upon consumption of the composition by a subject, the observed curcumin $AUC_{0-4}$ hours is at least 500 ng min/ml.

10. The composition of claim 1, wherein the composition comprises 200 mg of curcumin; and wherein upon consumption of the composition by a subject, the observed curcumin $AUC_{0-8}$ hours is at least 7,500 ng min/ml.

11. The composition of claim 1, wherein the composition comprises 100 mg of curcumin; and wherein upon consumption of the composition by a subject, the observed curcumin $C_{max}$ is at least about 7.5 ng/ml.

12. The composition of claim 1, wherein the composition increases gut solubility of the compound relative to the unformulated compound.

13. The composition of claim 1, wherein the composition increases enterocytic transport of the compound relative to the unformulated compound.

* * * * *